United States Patent [19]

Demmin et al.

[11] 4,311,850

[45] Jan. 19, 1982

[54] PREPARATION OF HIGHER MUCONIC ACID MONESTERS

[75] Inventors: Timothy R. Demmin, Randolph; Milorad M. Rogic, Whippany, both of N.J.

[73] Assignee: Allied Corporation, Morristown, N.J.

[21] Appl. No.: 95,710

[22] Filed: Nov. 19, 1979

Related U.S. Application Data

[62] Division of Ser. No. 1,990, Jan. 8, 1979, Pat. No. 4,208,341.

[51] Int. Cl.$^3$ .............................................. C07C 67/39
[52] U.S. Cl. .................................... 560/131; 560/61; 560/81; 560/144; 560/145; 560/146; 560/171; 560/181; 560/190; 560/192
[58] Field of Search ............... 560/145, 146, 198, 181, 560/192, 171, 81, 61, 131, 144, 190

[56] References Cited
PUBLICATIONS

Tsuji et al I, JACS 96(23), pp. 7349–7350, (1974).
Tsuji et al II, Tetrahedron Letters 17, pp. 1365–1366, (1976).
Tsuji et al III, Tetrahedron 34, pp. 641–644, (1978).
Rogic et al I, JACS 98(23), pp. 7441–7443, (1976).
Tsuji et al IV, Tetrahedron Letters, 14, pp. 1245–1246, (1975).
Rogic et al II, JACS, 100(17), pp. 5472–5487, (1978).
Takahashi et al, Synthetic Communications, 2(4), 181–184, (1972).

Primary Examiner—Natalie Trousof
Assistant Examiner—Frederick Pepper
Attorney, Agent, or Firm—Alan M. Doernberg

[57] ABSTRACT

Muconic acid monoesters of alkanediols of 2–6 carbons and of phenol are prepared by copper (II) oxidative cleavage of phenols, catechols or orthobenzoquinones. The products are useful as comonomers in polyamides and other polymers. The alkanediol or phenol is introduced into the copper (II) reactant or catalyst.

2 Claims, No Drawings

PREPARATION OF HIGHER MUCONIC ACID MONESTERS

This is a division, of application Ser. No. 1,990, filed Jan. 8, 1979, now U.S. Pat. No. 4,208,341.

BACKGROUND OF THE INVENTION

The oxidative cleavage of phenols, catechols and orthobenzoquinones with a reagent prepared from cuprous chloride, oxygen, pyridine and methanol is known. The product is the monomethyl ester of cis,cis muconic acid. The dimethyl ester of cis, cis muconic acid has also been prepared. It has been disclosed that monoesters can also be prepared by reacting catechols and 4-tert-butyl-1,2-benzoquinone with a copper (II) reagent generated from oxygen, cuprous chloride in pyridine and any of the following alcohols: methanol, ethanol, n-butyl alcohol and isopropyl alcohol.

BRIEF DESCRIPTION OF THE INVENTION

The present invention includes a copper (II) reagent prepared by reacting an alcohol selected from the group consisting of phenol and alkanediols of 2–6 carbons with a paired spin copper oxide having equimolar amounts of copper and oxygen and showing no absorption by Electron Spin Resonance, said copper (II) reagent having a relative minimum in the visible spectrum of about 565 nm and a relative maximum in the visible spectrum of about 730 nm.

The present invention also includes a method of producing muconic acid monoesters which comprises reacting a cyclic starting material selected from the group consisting of phenols of the formula

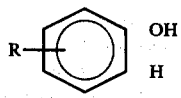

catechols of the formula

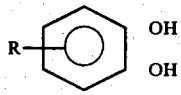

and orthobenzoquinones of the formula

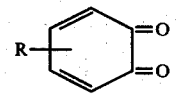

where R is H, alkyl, alkoxy, bromo, chloro, amino, phenyl or phenoxy with the above copper reagent and recovering the muconic monoester of said alcohol.

The present invention also includes as a composition of matter a monoester of a muconic acid and an alcohol selected from the group consisting of phenol and alkanediols of 2–6 carbons.

DETAILED DESCRIPTION OF THE INVENTION

The copper reagent of the present invention can be prepared as the product of reaction between a selected alcohol and a certain copper oxide. The copper oxide can, in turn, be produced by a variety of previously disclosed processes and by processes first disclosed herein. First, the oxidation of cuprous chloride with oxygen has been known to produce a reagent which, when combined with methanol, is active in cleaving cyclic starting materials such as catechol and phenol. Preparations in which this active reagent is found are believed to produce first a certain paired spin cyclic copper oxide and then, from reaction of methanol with the copper oxide, an active species thought of as cupric methoxy hydroxide. The evidence supporting this theory is described in our article at pages 5472–5487 of the Aug. 16, 1978 issue of Journal of the American Chemical Society. The paired spin copper oxide may also be prepared by oxidizing copper metal with oxygen in the presence of at least catalytic amounts of cuprous or cupric chloride (collectively copper chloride). Fine copper powder is slowly and continuously added, as is oxygen gas, to the copper chloride in an inert solvent such as pyridine. Since the copper chloride is not consumed, but instead the net reaction is one of converting the copper metal to the copper oxide, one can prepare a solution in increasing copper oxide/copper chloride ratios with increasing time. By contrast, the oxidation of cuprous chloride in pyridine produces a mixture of cupric chloride (as a pyridine complex) and the copper oxide in which substantially 50% of the copper is in each species, according to the following stoichiometry:

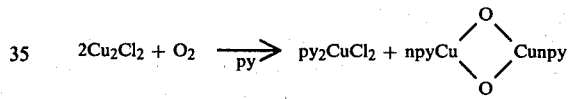

wherein py$_2$CuCl$_2$ represents the same cupric pyridine complex formed by dissolving cupric chloride in pyridine and the latter structure represents the paired spin copper oxide used in the present invention. This oxide is characterized by an equimolar content of oxygen and copper (as computed from the observed stoichiometry) but cannot be observed in Electron Spin Resonance spectroscopy. While copper (I) is diamagnetic and hence would not be observed by Electron Spin Resonance, the evidence (including acid hydrolysis of the oxide to cupric oxide) strongly suggests a copper (II) state in which copper atoms with opposite net spins are closely paired either as a tight di-u-oxo bridged copper (II) dimer, oligomer or a polymer. When formed in pyridine, this copper oxide is solvated or complexed by pyridine.

Any copper oxide having the above characteristics and which can react with methanol to form a reagent capable of cleaving catechol to cis,cis muconic acid monoester is suitable as a starting material in preparing the present copper reagents. It is preferred, however, that lower alcohols such as methanol, ethanol, isopropyl alcohol and n-butyl alcohol not be present while preparing the present copper reagents, as such alcohols compete with the diols and phenol of the present invention in reacting with the paired copper oxide.

The following reactions summarize some of the work reported in our Aug. 16, 1978 article establishing that the copper chloride is not the active cleavage reagent:

(1) CuCl + O₂ + pyridine + methanol "CuMe reagent"

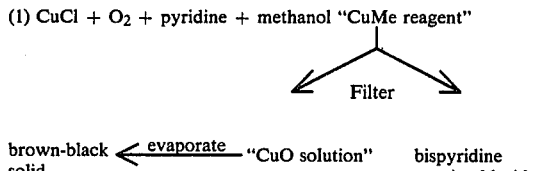

The same "CuMe reagent" can be prepared by adding methanol after consumption of oxygen or by adding water to (pyCuClOMe)₂. Any of the "CuMe reagent", the "CuO solution" and the resuspended brown-black solid are active to cleave catechol to form cis,cis muconic acid monomethyl ester. Neither the bispyridine cupric chloride recovered by filtration and resuspended, nor fresh bispyridine cupric chloride in pyridine, nor fresh bispyridine cupric chloride plus methanol was effective to cleave catechol, the former two giving no reaction and the latter giving 4,5-dimethoxy-1,2-benzoquinone.

Many of the methods so described are unpreferred in the present invention since methanol is present during formation of the paired spin copper oxide and will form the "CuMe reagent" competitively with the formation of the active copper (II) higher alcohol reagent.

Higher alcohols suitable for preparation of the present copper reagents include phenol and alkanediols of 2-6 carbons such as ethylene diol, 1,2-propanediol, 1,2-butanediol, 1,4-butanediol, 1,2-hexanediol and other diols of the formula HO—R—OH where R is straight or branched alkane of 2-6 carbons.

Cyclic starting materials suitable in the present invention include phenol, catechol and orthobenzoquinone. Monosubstituted forms of these three cyclic materials are also included with the substituent being alkyl, alkoxy, bromo, chloro, amino, phenyl or phenoxy. In the case of alkyl or alkoxy substituents straight or branched chain alkyl groups of 1-6 carbons are preferred.

As in the case of the oxidation of phenols in the presence of other copper reagents, oxygen must be present during the reaction if a phenol cyclic starting material is used. No oxygen is required in the case of catechol and benzoquinone cyclic starting materials provided that excess copper reagent is used. Otherwise the conditions for the cleavage reaction are not critical and are as described in our Aug. 18, 1978 article.

The products of the cleavage reaction are novel muconic acid monoesters of the formula:

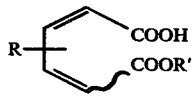

where R is as described above, R' is phenyl or HO—R"—, with R" being alkyl of 2-6 carbons. It will be appreciated that these acids may exist after reaction as copper salts, but may be recovered by acid hydrolysis and then separation from the remaining components by extraction with a suitable solvent or by a suitable form of chromatography.

These monoesters are themselves useful as comonomers, being polymerizable at both the unsaturation sites and the free acid site. Furthermore, upon hydrogenation with H₂ and Raney nickel (or other known catalyst), these monoesters can, in cases where R is hydrogen, be converted to adipic acid esters of the formula

HOOC—(CH₂)₄—COOR' where R' is as described above and can, in cases where R is not hydrogen, be converted to acid esters of the formula HOOC—(CH₂)₃(CHR)—COOR' where R and R' are as described above and the placement of (CHR) among (CH₂) groups is determined by the position of R on the muconic acid ester. Such adipic and other acid esters are desirable as chain terminators for polyamides such as nylon-6 and nylon-66, to produce polyamides having a terminal phenyl or hydroxy group. Where R' is phenyl, a good "leaving group" is available for further reaction (as by substitution or crosslinking) at this site on the polymer.

EXAMPLE 1—Muconic Acid Mono(4-hydroxybutyl) Ester from Catechol

A solution of cuprous chloride (2.00 g, 20 m mole) in dry pyridine (60 ml) was stirred under an atmosphere of molecular oxygen until approximately one equivalent (130 ml, 5.8 mmole) of oxygen was consumed in an oxidation reaction with stoichiometric proportions of cuprous chloride: oxygen of 4:1. 1,4-Butanediol (0.90 g, 10 mmole) was added next via syringe followed by the addition of a solution of catechol (0.55 g, 5 mmole) in pyridine (20 ml) over 45 minutes. With stirring an additional 45 minutes, the solution consumed 140 ml (6.25 mmoles) of oxygen. The pyridine was then evaporated and the residue hydrolyzed with 50 ml of 0.2 N aqueous HCl at 0° C. with rapid stirring in the presence of 250 ml of methylene chloride to produce an organic layer from which was recovered 0.25 g (23% yield) of crude muconic acid mono(4-hydroxybutyl) ester, melting point 92°-98° C. This product appeared to be the cis,cis isomer. Triturating with methylene chloride raised the apparent melting point to 107°-110° C. The properties of this product were as follows:

Infrared (nujol mull): 3425 (alcohol OH), 3400-2400 (—CO₂H), 1720, 1700, 1600, 1242, 1190 cm⁻¹.

PMR (Acetone -d₆) δ1.6-1.9 (m, 4H, —CH₂CH₂—C—O—), 3.57 (distorted t, J~6 Hz, 2H, —CH₂—OH), 4.13 (distorted t, J 6 Hz, 2H, —C(O)—O—CH₂—), 5.99 (sym m, 2H, =CH—CH=), 6.13 (b, ~2H, OH), 7.80 (sym m, 2H, =CH—C(O)—).

CMR (Acetone -d₆) δ26.07 (C—CH₂—C), 29.97 (C—CH₂—C), 61.91 (CH₂OH), 65.03 (O=C—O—CH₂), 124.89 (=CH—CO₂R), 125.47 (=CH—CO₂H), 138.36 (—CH=C—CO—, both beta-vinyl carbons), 166.10 (—CO₂R), CO₂H (not observed).

Mass spectroscopy (C.I./NH₃): 215 (M+H⁺), 232 (M+NH₄⁺).

EXAMPLE 2—Muconic Acid Monophenyl Ester

Cuprous chloride (1.00 g, 10 mmole) was oxidized in dry pyridine (30 ml) as in Example 1. A solution of phenol (0.47 g, 5 mmole) in 150 ml of pyridine was added over 5 minutes. The mixture was stirred for 21.5 hours and 190 ml (8.5 mmole) of molecular oxygen was consumed. After the mixture was thoroughly evaporated in vacuo (30° C., 0.5 mm of mercury pressure), the residue was stirred with diethyl ether (100 ml) and the insoluble copper salts filtered off. Evaporation of the ether gave only pyridine and a trace of phenyl.

The mixture of copper salts from the filtration were then stirred with 250 ml of methylene chloride at 0° C., and 50 ml of 2N HCl was added over 30 minutes. The organic layer was dried with magnesium sulfate and the solvent evaporated off to give 0.60 g of tan solid shown by nuclear magnetic resonance spectroscopy and gas chromatography analyses to be about 80% muconic acid monophenyl ester or an approximate 88% yield based on 100% conversion of phenol. The crude product also contained about 1% of an unidentified species with molecular weight of 190 and about 12% of another compound identified as 4-phenoxymuconic acid monophenyl ester. Muconic acid monophenyl ester, purified by recrystallizing the crude product from toluene and vacuum sublimation (100° C./0.05 mm of mercury) has a melting point of 126°–127° C. and the following properties:

$C_{12}H_{10}O_4$: Calculated: C, 66.05; H, 4.62. Found: C, 65.83; H, 4.65.

Infrared (nujol): 3500–2200, 1735, 1690, 1635, 1604, 1586, 1336, 878 and 683.

Mass Spectroscopy (C.I./CH$_4$) 219(M+H+), 247 (M+C$_2$H$_5$+CH$_3$CN):

Ultraviolet MAX: 263 nm ($\epsilon$22,700).

PMR (CDCl$_3$) $\delta$: 6.07 (d,J=11.5 Hz, 1H,=C$\underline{H}$—CO$_2$H), 6.35 (d,J=15.8 Hz, 1H,=CH—CO$_2$Ar), 6.83 (d,J=11.5 Hz,1H,—C$\underline{H}$=CH—CO$_2$H), ~6.9–7.8 (m,5H,—Ar), 8.57 (d of d, J~12 Hz, 15.8 Hz,1H,—CH=CH—CO$_2$Ar), 10.17 (bs, 1H, —CO$_2$H).

CMR (CDCl$_3$) $\delta$: 121.47, 128.99, 129.39 and 150.59 (—Ar), 124.49 (=C—CO$_2$Ar), 125.96 (=C—CO$_2$H), 139.80 (—C=C—CO$_2$Ar), 142.35 (—C=C—CO$_2$H), 164.35 (—CO$_2$Ar), 170.50 (—CO$_2$H).

The 4-phenoxymuconic acid monophenyl ester was purified by column chromatographic separation using Sephadex LH-20/methyl acetate and had a melting point of 162°–172° C. (short white needles) and was characterized by ultraviolet, infrared, PMR, CMR, element analysis and mass spectroscopy (M.W. 311 for M+H+).

EXAMPLE 3

Example 2 was repeated with 0.33 g (3.33 mmole) cuprous chloride in pyridine and 0.156 g (1.66 mmole) phenol in pyridine (total pyridine 100 ml) except that the phenol was added to the oxidized copper chloride with magnetic stirring in a glass lined reactor under an initial oxygen pressure of 60 psig (5 atmospheres). After four and one half hours there was no further pressure drop. Isolation and analysis as in Example 2 indicated a 76% yield of muconic acid monophenyl ester and 9–10% yield of 4-phenyoxymuconic acid monophenyl ester at 94% conversion of phenol.

We claim:

1. A method of producing muconic acid monophenyl ester which comprises reacting a cyclic starting material selected from the group consisting of phenol and catechol with a copper reagent prepared by reacting phenol with a paired spin copper oxide having equimolar amounts of copper and oxygen and showing no absorption by Electron Spin Resonance, said paired spin copper oxide having a relative minimum in the visible spectrum of about 565 nm and a relative maximum of about 730 nm, oxygen being present during the reaction when phenol is cyclic starting material; and recovering muconic acid monophenyl ester by acidification of the product of the reaction.

2. The method of claim 1 wherein said cyclic starting material is phenol and oxygen is present during the reaction.

* * * * *